US008753690B2

(12) United States Patent
Higgins et al.

(10) Patent No.: US 8,753,690 B2
(45) Date of Patent: Jun. 17, 2014

(54) METHODS AND COMPOSITIONS FOR DELIVERING INTERLEUKIN-1 RECEPTOR ANTAGONIST

(75) Inventors: Joel C. Higgins, Claypool, IN (US); Jennifer E. Woodell-May, Warsaw, IN (US); Jacy Hoeppner, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 784 days.

(21) Appl. No.: 12/549,015

(22) Filed: Aug. 27, 2009

(65) Prior Publication Data
US 2010/0055087 A1 Mar. 4, 2010

Related U.S. Application Data

(63) Continuation-in-part of application No. 12/394,723, filed on Feb. 27, 2009.

(60) Provisional application No. 61/031,803, filed on Feb. 27, 2008, provisional application No. 61/116,940, filed on Nov. 21, 2008, provisional application No. 61/155,048, filed on Feb. 24, 2009.

(51) Int. Cl.
*A61K 35/12* (2006.01)
*A61K 38/00* (2006.01)

(52) U.S. Cl.
USPC .......................... 424/574; 424/85.2; 514/1.1

(58) Field of Classification Search
CPC ....... A61K 35/35; A61K 38/00; C07K 14/47; C07K 14/7155
USPC .................... 424/85.1, 574; 514/1.1
See application file for complete search history.

(56) References Cited

U.S. PATENT DOCUMENTS

| | | | |
|---|---|---|---|
| 4,853,137 A | 8/1989 | Ersson | |
| 5,075,222 A | 12/1991 | Hannum et al. | |
| 5,571,418 A | 11/1996 | Lee et al. | |
| 5,585,007 A | 12/1996 | Antanavich et al. | |
| 5,788,662 A | 8/1998 | Antanavich et al. | |
| 5,792,450 A | 8/1998 | Wilson et al. | |
| 5,842,477 A | 12/1998 | Naughton | |
| 6,063,297 A | 5/2000 | Antanavich et al. | |
| 6,096,728 A | 8/2000 | Collins et al. | |
| 6,214,338 B1 | 4/2001 | Antanavich et al. | |
| 6,398,972 B1 | 6/2002 | Blasetti et al. | |
| 6,599,873 B1 | 7/2003 | Sommer et al. | |
| 6,623,472 B1 | 9/2003 | Reincke et al. | |
| 6,649,072 B2 | 11/2003 | Brandt et al. | |
| 6,713,246 B1 | 3/2004 | Reinecke et al. | |
| 6,759,188 B2 | 7/2004 | Reinecke et al. | |
| 6,790,371 B2 | 9/2004 | Dolocek | |
| 6,905,612 B2 | 6/2005 | Dorian et al. | |
| 7,011,852 B2 | 3/2006 | Sukavaneshvar et al. | |
| 7,179,391 B2 | 2/2007 | Leach et al. | |
| 7,223,346 B2 | 5/2007 | Dorian et al. | |
| 7,374,678 B2 | 5/2008 | Leach et al. | |
| 7,465,293 B2 | 12/2008 | Reinecke et al. | |
| 7,470,371 B2 | 12/2008 | Dorian et al. | |
| 7,553,413 B2 | 6/2009 | Dorian et al. | |
| 7,608,258 B2 | 10/2009 | Mishra | |
| 7,708,152 B2 | 5/2010 | Dorian et al. | |
| 7,901,344 B2 | 3/2011 | Yoo | |
| 7,914,689 B2 | 3/2011 | Higgins et al. | |
| 8,048,321 B2 | 11/2011 | Leach et al. | |
| 2001/0053764 A1 | 12/2001 | Sims et al. | |
| 2002/0077276 A1 | 6/2002 | Fredeking | |
| 2003/0091536 A1 | 5/2003 | Frisbie et al. | |
| 2003/0099650 A1 | 5/2003 | Ho et al. | |
| 2003/0205538 A1 | 11/2003 | Dorian et al. | |
| 2004/0120942 A1 | 6/2004 | McGinnis et al. | |
| 2004/0182795 A1 | 9/2004 | Dorian et al. | |
| 2004/0251217 A1 | 12/2004 | Leach et al. | |
| 2005/0084962 A1 | 4/2005 | Simon | |
| 2005/0109716 A1 | 5/2005 | Leach et al. | |
| 2005/0186120 A1 | 8/2005 | Dorian et al. | |
| 2005/0196874 A1 | 9/2005 | Dorian et al. | |
| 2005/0197293 A1 | 9/2005 | Mellis et al. | |
| 2006/0051865 A1 | 3/2006 | Higgins et al. | |
| 2006/0057693 A1 | 3/2006 | Simon | |
| 2006/0175242 A1 | 8/2006 | Dorian et al. | |

(Continued)

FOREIGN PATENT DOCUMENTS

| | | |
|---|---|---|
| EP | 2186877 | 5/2010 |
| WO | WO 99/67277 | 12/1999 |

(Continued)

OTHER PUBLICATIONS

Juge-Aubry et al. Regulatory Effects of Interleukin (IL)-1, Interferon-beta, and IL-4 on the Production of IL-1 Receptor Antagonist by Human Adipose Tissue. The Journal of Clinical Endocrinology & Metabolism 2004, 89(6):2652-2658.*
Arend, W. et al. "Interleukin-1 Receptor Antagonist: Role in Biology" Annu. Rev. Immunol., vol. 16 (pp. 27-55) 1998.
Biomet Biologics, Inc. "GPS® II Platelet Concentrate System: The New Gold Standard" Product Brochure (14 pages) Sep. 2006.
Biomet Biologics, Inc. "GPS® III Platelet Separation System" Product Brochure (8 pages) 2007.
Biomet Biologics, Inc. "Plasmax Plasma Concentrate" Product Brochure (6 pages) 2006.
Biomet Biologics, Inc. "Vortech Concentration System Product" Product Brochure (16 pages) Aug. 2005.
Biomet Biologics, Inc. "GPS System Shoulder Recovery with the GPS Platelet Concentrate System" Product Brochure (6 pages) 2004.
Cell Factor Technologies, Inc. "GPS® Platelet Concentrate System" Product Brochure (9 pages) 2004.

(Continued)

*Primary Examiner* — Taeyoon Kim
(74) *Attorney, Agent, or Firm* — Harness, Dickey

(57) ABSTRACT

Methods and compositions generating and using an interleukin-1 receptor antagonist (IL-1ra)-rich solution. Methods for generating and isolating interleukin-1 receptor antagonist include incubating adipose tissue and/or adipocytes with polyacrylamide beads to produce interleukin-1 receptor antagonist. The interleukin-1 receptor antagonist is isolated from the polyacrylamide beads to obtain the solution rich in interleukin-1 receptor antagonist. Methods for treating a site of inflammation in a patient include administering to the site of inflammation the solution rich in interleukin-1 receptor antagonist.

10 Claims, 7 Drawing Sheets

(56) References Cited

U.S. PATENT DOCUMENTS

| | | |
|---|---|---|
| 2006/0175244 A1 | 8/2006 | Dorian et al. |
| 2006/0175268 A1 | 8/2006 | Dorian et al. |
| 2006/0243676 A1 | 11/2006 | Swift et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0075016 A1 | 4/2007 | Leach |
| 2007/0092494 A1 | 4/2007 | Higgins et al. |
| 2007/0207161 A1 | 9/2007 | Ralph |
| 2007/0208321 A1 | 9/2007 | Leach et al. |
| 2008/0011684 A1 | 1/2008 | Dorian et al. |
| 2008/0064626 A1 | 3/2008 | Zanella |
| 2008/0193424 A1 | 8/2008 | McKale et al. |
| 2008/0217263 A1 | 9/2008 | Higgins et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2009/0014391 A1 | 1/2009 | Leach et al. |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0181019 A1 | 7/2009 | Solinger |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0125236 A1 | 5/2010 | Bare et al. |
| 2010/0140182 A1 | 6/2010 | Chapman |
| 2010/0256595 A1 | 10/2010 | Leach et al. |
| 2011/0052561 A1 | 3/2011 | Hoeppner |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0129441 A1 | 6/2011 | Lentz |
| 2011/0189172 A1 | 8/2011 | Solinger et al. |
| 2011/0268708 A1 | 11/2011 | Lin et al. |
| 2012/0027746 A1 | 2/2012 | Dorian et al. |
| 2012/0093936 A1 | 4/2012 | Lindenberg et al. |

FOREIGN PATENT DOCUMENTS

| | | |
|---|---|---|
| WO | WO 2004/009207 | 1/2004 |
| WO | WO 2007/121538 | 11/2007 |
| WO | WO 2007/128973 | 11/2007 |
| WO | WO 2011/031553 | 3/2011 |
| WO | WO 2012/030593 | 3/2012 |

OTHER PUBLICATIONS

Cell Factor Technologies, Inc., Biomet Europe. "GPS® II System, Gravitational Platelet Separation System, Accelerating the Body's Natural Healing Process" Product Bruchure (16 pages) 2005, http://www.cellfactortech.com/global_products.cfm, printed Sep. 16, 2005.

Cell Factor Technologies, Inc., Biomet Europe. "GPS® II System, Gravitational Platelet Separation System" User Manual (13 pages), http://www.cellfactortech.com/global_products.cfm, printed Sep. 16, 2005.

Dinarello, C. "Interleukin-1 and Interleukin-1 Antagonism" Blood, vol. 77, No. 8 (pp. 1627-1652) Apr. 1991.

Eppley, et al. "Platelet Quantification and Growth Factor Analysis from Platelet-Rich Plasma: Implications for Wound Healing," Plastic and Reconstructive Surgery, 114(6):1502-1508 (Nov. 2004).

Kaufman, A. et al. "Human macrophage response to UHMWPE, TiAlV, CoCr, and alumina particles: Analysis of multiple cytokines using protein arrays" Journal of Biomedical Materials Research Part A, published online in Wiley InterScience DOI: 10.1002/jbm.A. 31467 (pp. 464-474) Jul. 2007.

Matthews, J. et al. "Comparison of the response of primary human peripheral blood mononuclear phagocytes from different donors to challenge with model polyethylene particles of known size and dose" Biomaterials, vol. 21 (pp. 2033-2044) 2000.

Meier, H. et al. "The production of antiinflammatory cytokines in whole blood by physicochemical induction" Inflamm. Res., vol. 52 (pp. 404-407) Oct. 2003.

Muzio, M. et al. "Interleukin-13 Induces the Production of Interleukin-1 Receptor Antagonist (IL-1ra) and the Expression of the mRNA for the Intracellular (Keratinocyte) Form of IL-1ra in Human Myelomonocytic Cells" Blood, vol. 83, No. 7 (pp. 1738-1743) Apr. 1994.

Rader, C. et al. "Cytokine Response of Human Macrophage-like Cells After Contact With Polyethylene and Pure Titanium Particles" The Journal of Arthroplasty, vol. 14, No. 7 (pp. 840-848 (Oct. 1999).

Swift, M. et al. "Characterization of Growth Factors in Platelet Rich Plasma" Cell Factor Technologies, Inc. Printed Sep. 16, 2005 from www.cellfactortech.com/global_products.cfm.

Vangsness, T. et al. "Stimulation of IL-1ra Production from Platelet-Rich Plasma" Poster No. 488 presented at 54th Annual Meeting of the Orthopeadic Research Society in San Francisco, CA (1 page) Mar. 2-5, 2008.

Woodell-May, J. et al. "Effect of Incubation Time on Production of IL-1ra and sTNF-RI from Platelet-Rich Plasma" Paper No. 200, 55th Annual Meeting of the Orthopaedic Research Society (1 page) Feb. 2009.

Woodell-May, J. et al. "Elution of IL-1ra from a concentrated-plasma matrix—an in vitro study" Poster Presentation at 8th World Congress of the International Cartilage Repair Society, Miami, FL. (1 page) May 2009.

Woodell-May, J. et al. "Producing Accurate Platelet Counts for Platelet Rich Plasma: Validation of a Hematology Analyzer and Preparation Techniques for Counting" Scientific Foundation, Journal of Carniofacial Surgery, vol. 16, No. 5 (pp. 749-756) Sep. 2005.

Wright-Carpenter, T. "Treatment of Muscle Injuries by Local Administration of Autologous Conditioned Serum: A Pilot Study on Sportsmen with Muscle Strains" Int J Sports Med, vol. 25 (pp. 588-593) Oct. 2004.

Yang, S. et al. "Protective effects of IL-1Ra or vIL-10 gene transfer on a murine model of wear debris-induced osteolysis" Gene Therapy, vol. 11 (pp. 483-491) 2004.

Yang, T. et al. "Recent Applications of Polyacrylamide as Biomaterials" Recent Patents on Materials Science, vol. 1 (pp. 29-40) 2008.

Juge-Aubry, C. et al. "Adipose Tissue is a Major Source of Interleukin-1 Receptor Antagonist" Diabetes, vol. 52, May 2003 (pp. 1104-1110).

Bendele et al. "Combination of benefit of treatment with the cytokine inhibitors interleukin-1 receptor antagonist and PEGylated soluble tumor necrosis factor receptor type I in animal models of rheumatoid arthritis" Arthritis & Rheumatism, vol. 43, No. 12, Dec. 2000, pp. 2648-2659.

Bio-Rad Laboratories. Bio-Gel P Polyacrylamide Gel Instruction Manual, Obtained from www.bio-rad.com/webmaster/pdfs/9154_Bio-Gel_P.pdf on Jun. 20, 2012 (14 pages).

Burnouf, T. "Blood-derived, tissue engineering biomaterials" Biomedical Engineering—Applications, Basis & Communications, vol. 16, No. 6, Dec. 2004 (pp. 294-304).

Dallari et al. "Enhanced Tibial Osteotomy Healing with Use of Bone Grafts Supplemented with Platelet Gel or Platelet Gel and Bone Marrow Stromal Cells" The Journal of Bone and Joint Surgery, vol. 89 (2007) pp. 2413-2420.

Kim, Seon Hee et al. "Ex vivo gene delivery of Il-1Ra and soluble TNF receptor confers a distal synergistic therapeutic effect in anti-gen-induced arthritis", Molecular Therapy, vol. 6, No. 5, Nov. 1, 2002 (pp. 591-600).

Lucarelli, E. et al. "Platelet-derived growth factors enhance proliferation of human stromal stem cells" Biomaterials, vol. 24 (2003) pp. 3095-3100.

Morizaki et al. "The Effects of Platelet-Rich Plasma on Bone Marrow Stromal Cell Transplants for Tendon Healing in Vitro" J. Hand Surg. Am., vol. 35, No. 11 (Nov. 2010) pp. 1833-1841.

\* cited by examiner

METHODS AND COMPOSITIONS FOR DELIVERING INTERLEUKIN-1 RECEPTOR ANTAGONIST

CROSS-REFERENCE TO RELATED APPLICATIONS

This application is a continuation-in-part of U.S. patent application Ser. No. 12/394,723 filed on Feb. 27, 2009 which claims the benefit of U.S. Provisional Application No. 61/031,803, filed on Feb. 27, 2008; U.S. Provisional Application No. 61/116,940, filed on Nov. 21, 2008; and U.S. Provisional Application No. 61/155,048, filed on Feb. 24, 2009. The entire disclosures of each of the above applications are incorporated herein by reference.

INTRODUCTION

The present technology relates to compositions comprising interleukin-1 receptor antagonist, and methods for generating, isolating, and delivering such compositions.

Interleukin-1 (IL-1) includes a family of cytokines that can stimulate lymphocytes and macrophages, activate phagocytes, increase prostaglandin production, contribute to degeneration of bone joints, increase bone marrow cell proliferation, and are involved in many chronic inflammatory conditions. IL-1 can be generated by macrophages, monocytes, and dendritic cells, and can be part of the inflammatory response against infection.

The mode of action of IL-1 can be mediated by interleukin-1 receptor antagonist protein (IL-1ra; also known as "IRAP"). IL-1ra binds to the same receptor on the cell surface as IL-1, and thus prevents IL-1 from sending a signal to that cell. IL-1ra is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1ra is stimulated by several substances including adherent immunoglobulin G (IgG), other cytokines, and bacterial or viral components. IL-1ra is an important natural anti-inflammatory protein in arthritis, colitis, and granulomatous pulmonary disease.

IL-1ra can be used in the treatment of rheumatoid arthritis, an autoimmune disease in which IL-1 plays a key role, reducing inflammation and cartilage degradation associated with the disease. For example, Kineret™ (anakinra) is a recombinant, non-glycosylated form of IL-1ra (Amgen Manufacturing, Ltd., Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Application Publication No. 2005/0197293, Mellis et al., published Sep. 8, 2005 In addition, methods for producing IL-1ra from body fluids, including the use of autologous fluids, are described in U.S. Pat. No. 6,623,472, Reincke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004.

Compositions and methods using IL-1ra are known in the art. For example, IL-1ra has been delivered as part of a composition with hyaluronic acid, as described in U.S. Pat. No. 6,096,728, Collins et al., issued Aug. 1, 2000. However, many such methods and compositions are associated with issues regarding stability and half-life of IL-1ra as well as the amount and rate of IL-1ra provided. Accordingly, improved methods of delivering IL-1ra are desirable and would be useful in treating conditions and pathologies mediated by the interleukin-1 receptor, including the management of inflammation.

SUMMARY

The present technology provides methods for generating solutions rich in interleukin-1 receptor antagonist and for administering such solutions to the site of inflammation in a human or animal subject. Methods for generating such solutions include incubating adipose tissue with polyacrylamide beads. A solution rich in interleukin-1 receptor antagonist is then separated from the polyacrylamide beads. The adipose tissue may be obtained from the subject.

Methods of treating a condition mediated by the interleukin-1 receptor in a human or animal subject, such as inflammation, include co-administering a solution rich in interleukin-1 receptor antagonist and fibrinogen. In various embodiments, such methods further comprise administration of thrombin and calcium chloride to the subject. The site of inflammation may be associated, for example, with arthritis, e.g., osteoarthritis. Preferably, the solution of IL-1ra is autologous.

BRIEF DESCRIPTION OF THE DRAWINGS

The present technology will become more fully understood from the detailed description and the accompanying drawings, wherein.

Figure 1:
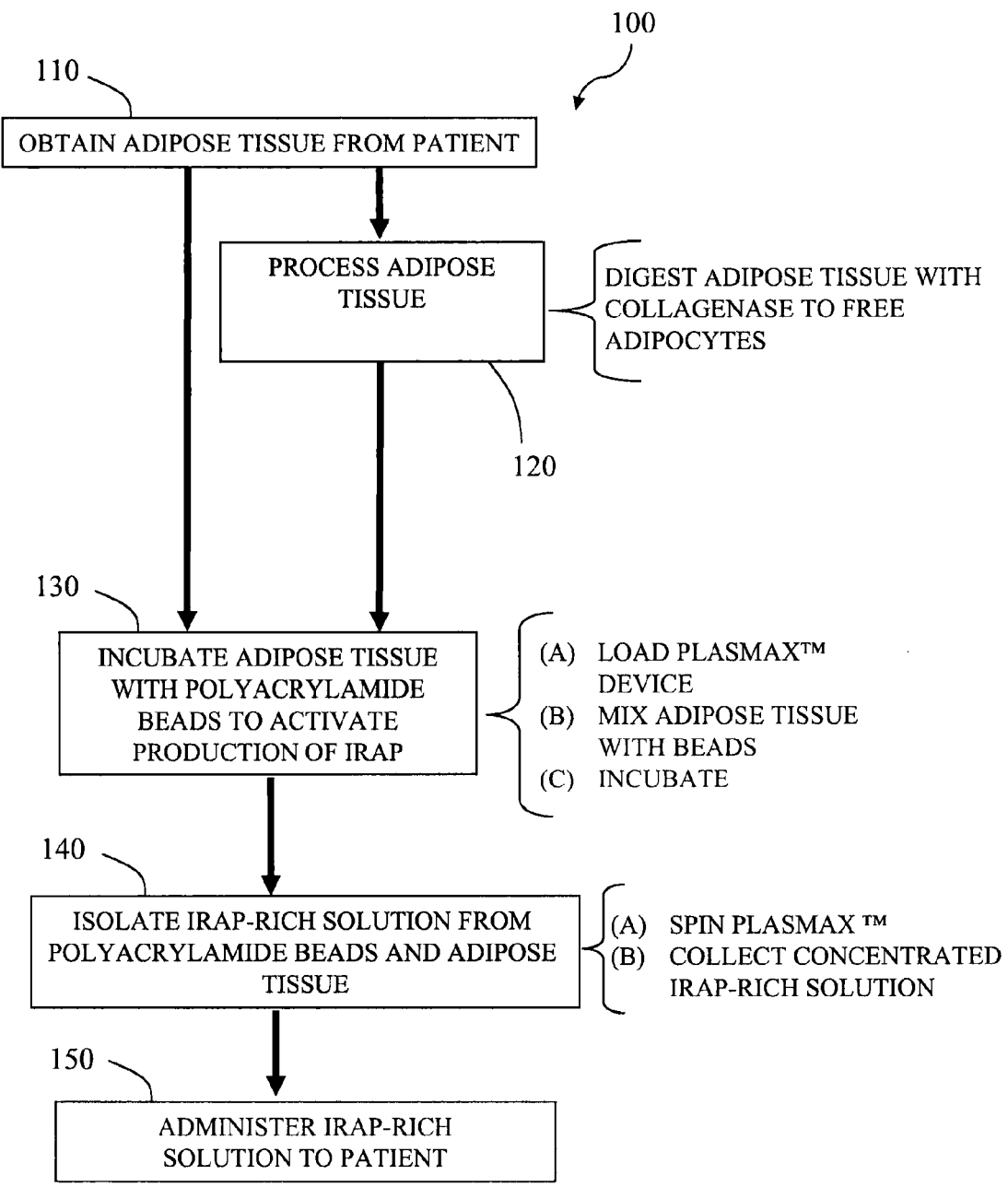
FIG. 1 is a diagrammatic illustration of a first method to produce a solution of IL-1ra according to an embodiment of the present technology.

It should be noted that the figures set forth herein are intended to exemplify the general characteristics of materials and methods among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The description of the following technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present technology relates to interleukin-1 receptor antagonist (IL-1ra), including methods of generating IL-1ra, compositions comprising IL-1ra produced by such methods, methods of using IL-1ra, treatment methods comprising IL-1ra, and devices for the generation, isolation, and administration of IL-1ra.

Methods for generating a solution rich in interleukin-1 receptor antagonist can include the following aspects. In some embodiments, methods for generating a solution rich in interleukin-1 receptor antagonist include contacting a liquid volume comprising adipocytes with polyacrylamide beads and separating the liquid volume from the polyacrylamide beads and the adipocytes to obtain a solution rich in interleukin-1 receptor antagonist. Without limiting the mechanism, utility, or function of the present technology, the polyacrylamide beads appear to serve as an activator of IL-1ra production by adipocytes. In some respects, contact of the adipocytes with the surface of the polyacrylamide beads appears to stimulate IL-1ra production and secretion by adipocytes. There also appears to be a correlation between the amount of IL-1ra produced and the concentration of white blood cells, where adipose tissue can include white blood cells. Thus, the present technology uses adipose tissue and disaggregated adipose tissue to obtain adipocytes, where white blood cells can be present in both the adipose tissue and the adipocytes obtained from adipose tissue.

The methods can further include the following aspects. The liquid volume of adipocytes can be part of isolated adipose tissue; where, for example, the adipose tissue may include other cell types. Contacting of the adipocytes and polyacrylamide beads may include incubating the liquid volume of adipocytes with the polyacrylamide beads for times ranging from about 30 seconds to about 24 hours. The contacting may also include contacting a liquid volume comprising white blood cells with the polyacrylamide beads, in addition to contacting the liquid volume of adipocytes with the polyacrylamide beads. The liquid volume of white blood cells can be whole blood, platelet rich plasma, or whole blood and platelet rich plasma. White blood cells can also be obtained from bone marrow. In some embodiments, separation to obtain the solution rich in interleukin-1 receptor antagonist comprises centrifuging the liquid volume of adipocytes and polyacrylamide beads to obtain a supernatant comprising the solution rich in interleukin-1 receptor antagonist. The resulting solution rich in interleukin-1 receptor antagonist can include from about 30,000 pg/mL to about 110,000 pg/mL interleukin-1 receptor antagonist.

In some embodiments, methods are provided for generating a solution rich in interleukin-1 receptor antagonist that is useful for treating an inflammatory disorder in a patient. These methods include obtaining adipose tissue from the patient and loading the adipose tissue into a concentrator assembly, where the concentrator assembly includes polyacrylamide beads. The mixture of polyacrylamide beads and adipose tissue is incubated to form a solution of interleukin-1 receptor antagonist. The concentrator assembly is then rotated at centrifugal speeds to separate the interleukin-1 receptor antagonist from the polyacrylamide beads and adipose tissue to obtain the solution rich in interleukin-1 receptor antagonist. Loading of the concentrator assembly may include incubating the adipose tissue with the polyacrylamide beads for a time of from about 30 seconds to about 24 hours.

The loading may further include loading a liquid volume comprising white blood cells into the concentrator assembly. The liquid volume of white blood cells can be in the form of whole blood, platelet rich plasma, or a combination of whole blood and platelet rich plasma.

The present technology also includes methods of treating one or more sites of inflammation in a patient. Such methods include contacting a liquid volume comprising adipocytes with polyacrylamide beads. The liquid volume is then separated from the polyacrylamide beads and the adipocytes to provide a solution rich in interleukin-1 receptor antagonist. The solution rich in interleukin-1 receptor antagonist is administered one or more sites of inflammation in the patient. The adipose tissue used may be derived from the patient; i.e., autologous. The method can be applied to treat inflammation associated with osteoarthritis.

In some embodiments, the present methods include administering fibrinogen, thrombin, and calcium to the site of inflammation in addition to administering the solution rich in interleukin-1 receptor antagonist. For example, methods can include co-administering (i) a first solution comprising the interleukin-1 receptor antagonist and fibrinogen, and (ii) a second solution comprising thrombin and calcium.

Thrombin used in the present methods may be made by a process that includes loading whole blood or plasma and a calcium solution into a blood isolation device. The whole blood or plasma is heated for at least about 20 minutes, at a temperature of at least about 20° C. Thrombin is isolated by centrifuging the heated whole blood or plasma. The whole blood or plasma may be obtained from the patient.

Also provided are methods of treating an inflammatory disorder in a patient. Such methods include obtaining adipose tissue from the patient and loading the adipose tissue into a concentrator assembly, where the assembly includes polyacrylamide beads. The mixture of beads and adipose tissue is incubated to form a solution of interleukin-1 receptor antagonist. The concentrator assembly is then rotated at centrifugal speeds to separate the interleukin-1 receptor antagonist from the polyacrylamide beads and obtain a solution rich in interleukin-1 receptor antagonist. Whole blood is obtained from the patient and loaded, along with a calcium solution, into a blood isolation device. The whole blood is heated for at least about 20 minutes at a temperature of at least about 20° C. The heated whole blood centrifuged to obtain a clotting fraction. The solution rich in interleukin-1 receptor antagonist and the clotting fraction are then administered to the site of the inflammation in the patient.

Treatment methods can further include the following aspects. Loading of the adipose tissue into the concentrator assembly, where the assembly includes polyacrylamide beads, can include loading a liquid volume comprising white blood cells with the adipose tissue into and incubating the mixture of beads, adipose tissue, and white blood cells to form a solution of interleukin-1 receptor antagonist. The liquid volume of white blood cells can be whole blood, platelet rich plasma, or whole blood and platelet rich plasma. Fibrinogen may also be administered to the site of the inflammation in the patient along with the solution rich in interleukin-1 receptor antagonist and the clotting fraction. The methods can be used to treat inflammation due at least in part to osteoarthritis.

Referring now to FIG. 1, a diagrammatic illustration is shown of a method 100 for generating a solution rich in IL-1ra. Adipose tissue is isolated from a patient at step 110. This adipose tissue may be used directly in step 130, or may be processed to provide adipocytes in step 120.

Adipose tissue refers to any fat tissue, either white or brown adipose tissue, which may be derived from subcutaneous, omental/visceral, mammary, gonadal, or other adipose tissue sites. In some embodiments, adipose tissue is derived from human subcutaneous fat isolated by suction assisted lipectomy or liposuction. Adipocytes may be isolated and/or freed from the adipose tissue and/or tissue portions using any suitable method, including methods known in the art such as mechanical and breakdown centrifugation. Adipocytes can also be isolated using enzymatic digestion. For example, adipocytes can be isolated from lipoaspirate, treated by sonication and/or enzymatic digestion, and enriched by centrifugation. Adipocytes isolated from adipose tissue may be washed and pelleted.

Methods for isolating adipose tissue and adipocytes can include the following aspects. About 50 cc of adipose tissue is collected by suction-assisted tumescent liposuction inside a specialized collection container attached to suction hoses and to a liposuction cannula. The collection container can have a gauze-type grid filter that allows the tumescent fluid to pass through and retains the solid adipose tissue. After collecting the adipose tissue, the collection container is removed from the suction device and reattached to a centrifugation device. The filter unit may further contain a filter having approximately a 100 micrometer pore size. Once the collection container containing the adipose tissue is attached to the centrifugation device, the tissue is sonicated. After sonication, the entire apparatus is inserted into a centrifuge bucket and centrifuged at, for example, 300×g for 5 minutes. After centrifugation, the collection container together with the filter unit is detached and can be discarded. The pellet containing the adipocytes can then be resuspended in biocompatible solutions, such as autologous plasma, plasma concentrate and platelet rich plasma.

Adipose tissue may also be treated with digestive enzymes and with chelating agents that weaken the connections between neighboring cells, making it possible to disperse the tissue into a suspension of individual cells, including adipocytes, without appreciable cell breakage. Following disaggregation, the adipocytes may be isolated from the suspension of cells and disaggregated tissue.

Various methods and devices for isolating and/or fractionating adipose tissue include those as described by U.S. Pat. Nos. 7,374,678 and 7,179,391 to Leach et al. and U.S. Pub. Nos. 2009/0014391, 2008/0283474, and 2007/0208321 to Leach et al. A device, such as the GPS™ Platelet Concentrate System (Biomet, Warsaw, Ind.), may be used to isolate adipocytes. These methods may include obtaining adipocytes by performing lipoaspiration on the patient to obtain adipose tissue, enzymatically digesting the adipose tissue, and separating and/or washing the adipocytes using these devices.

As shown at step 130 of FIG. 1, the adipose tissue and/or adipocytes are contacted with polyacrylamide beads. In some embodiments, the adipose tissue and/or adipocytes are incubated with the polyacrylamide beads for a time effective to remove a portion of the liquid in the liquid volume of white blood cells and platelets. The incubation may be carried out over a period from about 30 seconds to about 72 hours and may be carried out at a temperature from about 20° C. to about 41° C. For example, the incubation may be from about one minute to about 48 hours, from about 5 minutes to about 12 hours, or from about 10 minutes to about 6 hours. In some embodiments, the incubation is conducted at about 37° C. In some embodiments the adipose tissue and/or adipocytes are not incubated, but is contacted with the polyacrylamide beads for only so long as necessary to perform subsequent processing. The contacting may occur at ambient conditions, e.g., at a temperature of about 20-25° C.

Polyacrylamide beads used in step 130 can be formed by polymerizing acrylamide monomer using controlled and standardized protocols as known in the art to produce relatively uniform beads formed of polyacrylamide gel. In general, polyacrylamide is formed by polymerizing acrylamide with a suitable bifunctional crosslinking agent, most commonly N,N-methylenebisacrylamide (bisacrylamide). Gel polymerization is usually initiated with ammonium persulfate and the reaction rate is accelerated by the addition of a catalyst, such as N,N,N',N'-tetramethylethylenediamine (TEMED). In various embodiments, polyacrylamide beads comprise 0.5 micromole of carboxyl groups per milliliter of beads, imparting a slight anionic character (negative charge). The beads are also typically resistant to changes in pH, and are stable in many aqueous and organic solutions. By adjusting the total acrylamide concentration, the polyacrylamide gel can be formed in a wide range of pore sizes. Moreover, the polyacrylamide beads can be formed in many sizes and can have relatively uniform size distributions. Bead size may range from several micrometers in diameter to several millimeters in diameter. For example, various types of Bio-Gel™ P polyacrylamide gel beads (Bio-Rad Laboratories, Hercules, Calif., USA) have particle sizes ranging from less than about 45 µm up to about 180 µm. Polyacrylamide beads are also available from SNF Floerger (Riceboro, Ga., USA), Pierce Biotechnology, Inc. (Rockford, Ill., USA), and Polymers, Inc. (Fayetteville, Ark., USA).

Once polymerized, polyacrylamide beads can be dried and stored in a powder-like form. The dry beads are insoluble in water but can swell considerably upon being rehydrated. Rehydration returns the polyacrylamide beads to a gel consistency that can be from about two to about three times the dry state size. Thus, dry polyacrylamide beads may be used to absorb a portion of a liquid volume, including solutes smaller than the bead pore size, and can serve to concentrate the IL-1ra produced by the adipocytes and/or adipose tissue. For example, combining dry polyacrylamide beads with the adipocytes and/or adipose tissue in step 130 activates production of IL-1ra and also reduces the total liquid volume as the dry beads rehydrate and swell.

Without limiting the mechanism, utility or function of the present technology, the polyacrylamide beads may serve as an activator of IL-1ra production by adipocytes. Therefore, in the case of dry polyacrylamide beads, not only is liquid being absorbed from the volume of adipocytes, thereby concentrating the IL-1ra formed, but the beads further serve as a surface to stimulate IL-1ra production by the adipocytes. It appears that the increase in the amount of IL-1ra is not due to simply increasing the concentration by reducing the volume of the sample, but is due to activation of the adipocytes by the polyacrylamide beads to increase production and/or release of IL-1ra.

In some embodiments, a liquid volume comprising white blood cells, such as platelet-rich plasma and/or whole blood, may also be added to the polyacrylamide beads and adipose tissue and/or adipocytes in order to generate IL-1ra. Blood can be centrifuged to isolate platelet-rich plasma (PRP) containing white blood cells and platelets, which may be located in the buffy coat layer following sedimentation. One example of a device that may be used for isolating platelet-rich plasma at step 120 is shown in FIG. 2.

Figure 2:
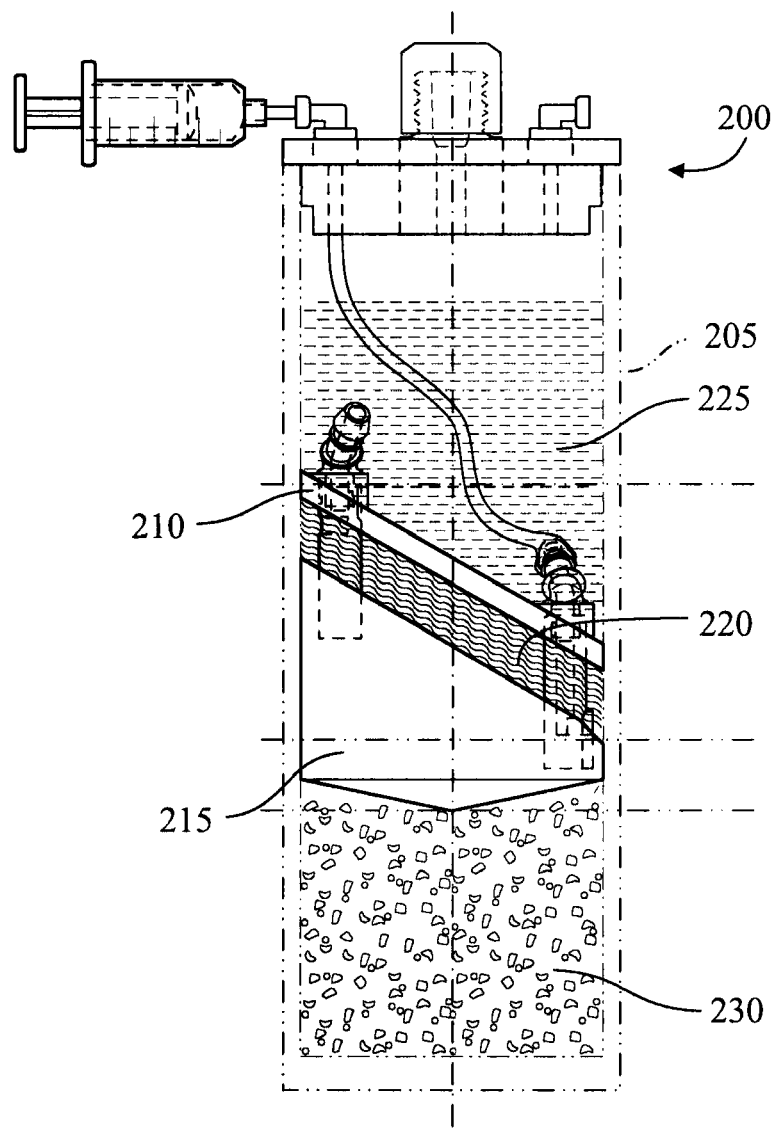
FIG. 2 is a partial cross-sectional view of a representative device used for isolating a liquid volume comprising white blood cells and platelets according to one embodiment of the present technology.

In this regard, the device 200 shown in FIG. 2 includes a container 205, such as a tube, that is placed in a centrifuge after being filled with blood. The container 205 includes a buoy system having an isolator 210 and a buoy 215. The buoy 215 has a selected density which is tuned to reach a selected equilibrium position upon centrifugation; this position lies between a more dense blood fraction and a less dense blood fraction. During centrifugation, the buoy 215 separates the blood within the container 205 into at least two fractions, without substantially commingling the fractions, by sedimenting to a position between the two fractions. In this regard, the isolator 210 and the buoy 215 define a layer comprising platelet-rich plasma 220, while less dense platelet-poor plasma 225 generally fractionates above the isolator 210, and more dense red blood cells 230 generally fractionate below the buoy 215. Following centrifugation, a syringe or tube may then be interconnected with a portion of the buoy system to extract the platelet-rich plasma, containing white blood cells. In various embodiments, such devices may be used to generate platelet-rich plasma that includes a platelet concentration up to about 8-fold higher than whole blood and a white blood cell concentration up to about 5-fold higher than whole blood. The platelet rich plasma may comprise from about 80% to about 90% of the white blood cells present in the whole blood. Such devices that are commercially available include the GPS® II Platelet Concentrate System, from Biomet Biologics, LLC (Warsaw, Ind., USA) and GPS® III Platelet Separation System, from Biomet Biologics, LLC (Warsaw, Ind., USA).

Devices that may be used to isolate platelet-rich plasma at step 120 are also described, for example, in U.S. Pat. No. 6,398,972, Blasetti et al., issued Jun. 4, 2002; U.S. Pat. No. 6,649,072, Brandt et al., issued Nov. 18, 2003; U.S. Pat. No. 6,790,371, Dolocek, issued Sep. 14, 2004; U.S. Pat. No. 7,011,852, Sukavaneshvar et al., issued Mar. 14, 2006; U.S. Application Publication No. 2004/0251217, Leach et al., published Dec. 16, 2004 (incorporated by reference herein); U.S. Application Publication No. 2005/0109716, Leach et al., published May 26, 2005 (incorporated by reference herein); U.S. Application Publication No. 2005/0196874, Dorian et al., published Sep. 8, 2005 (incorporated by reference herein); and U.S. Application Publication No. 2006/0175242, Dorian et al., published Aug. 10, 2006 (incorporated by reference herein).

Other methods may be used to isolate platelet-rich plasma. For example, whole blood can be centrifuged without using a buoy system, whole blood may be centrifuged in multiple stages, continuous-flow centrifugation can be used, and filtration can also be used. In addition, a blood component including platelet-rich plasma can be produced by separating plasma from red blood cells using a slow speed centrifugation step to prevent pelleting of the platelets. In other embodiments, the buffy coat fraction formed from centrifuged blood can be separated from remaining plasma and resuspended to form platelet-rich plasma.

In addition to the GPS® Platelet Concentrate and Separation Systems, a variety of other commercially available devices may be used to isolate platelet-rich plasma at step 120, including the Magellan™ Autologous Platelet Separator System, commercially available from Medtronic, Inc. (Minneapolis, Minn., USA); SmartPReP™, commercially available from Harvest Technologies Corporation (Plymouth, Mass., USA); DePuy (Warsaw, Ind., USA); the AutoloGel™ Process, commercially available from Cytomedix, Inc. (Rockville, Md., USA); the GenesisCS System, commercially available from EmCyte Corporation (Fort Myers, Fla., USA); and the PCCS System, commercially available from Biomet 3i, Inc. (Palm Beach Gardens, Fla., USA).

Blood drawn from the patient may be mixed with an anticoagulant. Suitable anticoagulants include heparin, citrate phosphate dextrose (CPD), ethylenediaminetetraacetic acid (EDTA), anticoagulant citrate dextrose solution (ACD), and mixtures thereof. The anticoagulant may be placed in the syringe used for drawing blood from the subject, or may be mixed with the blood after it is drawn.

White blood cells may also be prepared using other methods known in the art. For example, white blood cells may be prepared from whole blood by lysing red blood cells or by centrifugation of whole blood utilizing a density gradient where the white blood cells sediment to the bottom of a centrifuge tube. An example of density centrifugation includes the Ficoll-Paque™ Plus (GE Healthcare Bio-Sciences, Piscataway, N.J., USA). In some cases, a density gradient may be used to further separate mononuclear and polymorphonuclear cells. White blood cells may also be prepared from whole blood using filtration; an example includes the Acelere™ MNC Harvest System (Pall Life Sciences, Ann Arbor, Mich., USA). White blood cells can also be obtained from bone marrow.

Referring again to FIG. 1, following incubation with the polyacrymide beads, an IL-1ra-rich solution is isolated from the polyacrymide beads and adipose tissue and/or adipocytes, as indicated at step 140. Isolation may be accomplished by drawing off the liquid volume and leaving the beads. In some cases, the beads may be sedimented by centrifugation prior to drawing off the IL-1ra-rich solution. Isolation may also be performed by filtration, where the polyacrylamide beads are retained by a filter and the IL-1ra-rich solution passes through the filter using centrifugal force or by using vacuum, for example. If the incubation with polyacrylamide beads at step 130 utilizes dry polyacrylamide beads, the liquid volume may be reduced as the beads swell upon rehydration, thereby concentrating the resulting IL-1ra-rich solution. To maintain the increased concentration, care should be taken in the isolation step 140 so as to avoid compressing the beads or drawing liquid out from the swollen beads. For example, high centrifugal force or high vacuum may collapse the beads and/or draw liquid out of the internal volume of the beads.

In some cases, the incubation with polyacrylamide beads, as per step 130, and the isolation of the resulting IL-1ra-rich solution, as per step 140, may be performed using a single device. An example of a device for incubating adipose tissue and/or adipocytes with polyacrylamide beads is shown in FIGS. 3A and 3B. In this regard, the device 300 has an upper chamber 305 and a lower chamber 310. The upper chamber 305 has an end wall 315 through which the agitator stem 320 of a gel bead agitator 325 extends. The device 300 also has an inlet port 330 that extends through the end wall 315 and into the upper chamber 305. The device 300 also includes an outlet port 335 that communicates with a conduit 340. The floor of upper chamber 305 includes a filter 345, the upper surface of which supports desiccated concentrating polyacrylamide beads 350.

During use, a fluid 355 containing adipose tissue and/or adipocytes is injected to the upper chamber 305 via the inlet port 330 and mixed with the polyacrylamide beads 350. The fluid 355 and polyacrylamide beads 350 may be mixed by rotating the agitator stem 320 and the gel bead agitator 325, to help mix the fluid 355 and beads 350. The mixed fluid 355 and polyacrylamide beads 350 are then incubated for the desired time at the desired temperature. The device 300 is then centrifuged so that liquid passes to the lower chamber 310 while the polyacrylamide beads 350 are retained by a filter 345, thereby separating the polyacrylamide beads 350 from the resulting solution 360 of IL-1ra that collects in the lower chamber 310. The solution 360 may be removed from the device via outlet port 335.

Figure 3:
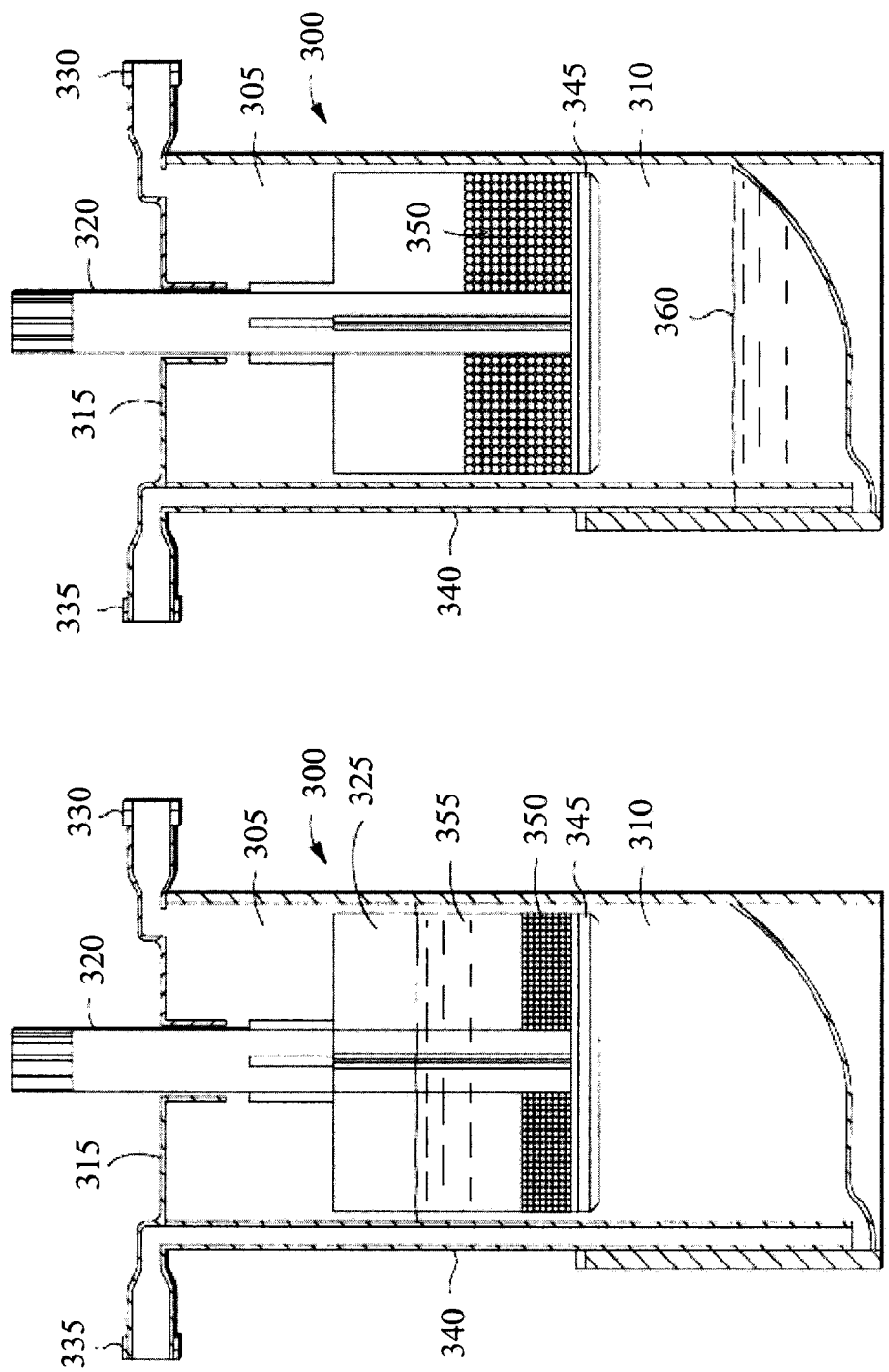
FIGS. 3A and 3B are cross-sectional views of a representative device for incubating a volume of white blood cells and platelets with polyacrylamide beads according to one embodiment of the present technology.

Exemplary devices of FIG. 3 are disclosed in U.S. Application Publication 2006/0175268, Dorian et al., published Aug. 10, 2006; and U.S. Application Publication 2006/0243676, Swift et al., published Nov. 2, 2006; both of which are incorporated by reference herein. Such a device is commercially available as Plasmax™ Plus Plasma Concentrator, from Biomet Biologics, LLC (Warsaw, Ind., USA).

Referring again to FIG. 1, in step 150 the IL-1ra-rich solution is administered to a human or animal subject (patient). The patient receiving the IL-1ra-rich solution may be the same patient from which the adipose tissue in step 110 is derived. In this case, the method provides an autologous preparation of IL-1ra. Administration may be performed using various means, such as by injection of the IL-1ra-rich solution using a syringe, surgical application, or application concomitant with another surgical procedure. It should be understood, however, that step 150 may comprise any biomedically acceptable process or procedure by which the IL-1ra-rich solution is implanted, injected, or otherwise administered in or in proximity to a site in order to mediate effects related to stimulation of the interleukin-1 receptor, such as inflammation and inflammation due to osteoarthritis. For example, for treating inflammation caused by arthritis, an autologous IL-1ra-rich solution may be administered to the patient via injection. Injection may be located at or into the synovial space of an inflamed joint, or otherwise at or near the joint.

The various preparations of IL-1ra-rich solutions produced by the present technology may be sterilized by including a sterile filter to process the final isolated IL-1ra product. Similarly, an antibiotic may be included in the polyacrylamide beads during incubation or added at one or more of the various steps in the methods described herein.

The present technology provides improved methods for preparing solutions rich in IL-1ra, including autologous IL-1ra-rich concentrated plasma solutions, which reduce and/or substantially eliminate immunological issues that may arise when using non-autologous material or recombinant material. In addition, since the IL-1ra is produced by the patient's cells, natural post-translational modifications, such as glycosylation, are already present. This is not the case with most recombinant proteins since they are produced in prokaryotic hosts.

Solutions rich in IL-1ra generated by the present technology can be characterized as having increased concentrations of IL-1ra relative to the concentration of IL-1ra typically found in whole blood. For example, the present methods and compositions can include about 34,000 pg/mL to about 108,000 pg/mL of IL-1ra, whereas whole blood can include about 200 pg/mL to about 800 pg/mL. It is understood, however, the concentrations present in any given solution may vary depending on the initial levels of components present in the adipose tissue, adipocytes, and/or source of white blood cells used in the present methods, and that increases in concentration are relative to those initial levels. In general, IL-1ra is present in the present solutions at concentrations of at least about 10,000 pg/ml, at least about 25,000 pg/ml, or at least about 30,000 pg/ml and can be up to 108,000 pg/mL or more.

The IL-1ra-rich solutions may be administered to mediate effects of IL-1 and attenuate signaling via the interleukin-1 receptor. The IL-1ra-rich solution may be used to block the biologic activity of naturally occurring IL-1, including inflammation and cartilage degradation associated with arthritis, by competitively inhibiting the binding of IL-1 to the interleukin-1 type receptor, which is expressed in many tissues and organs. For example, bone resorption and tissue damage such as cartilage degradation as a result of loss of proteoglycans due to IL-1 may be treated by administration of the IL-1ra-rich solution. In patients with arthritis, endogenous IL-1ra may not be found in effective concentrations in synovium and synovial fluid to counteract IL-1 concentrations in these patients, and hence the present IL-1ra-rich solution may be administered to treat these conditions and these sites. Dosing, administration, and frequency of treatment may be modified based on established medical practices to achieve effective treatment.

Referring again to FIG. 1, in step 150 the IL-1ra-rich solution is administered to a human or animal subject (i.e., a patient). The patient receiving the IL-1ra-rich solution may be the same patient from which the adipose tissue in step 110 is derived. In this case, the method provides an autologous preparation of IL-1ra. Administration may be performed using various means, such as by injection of the IL-1ra-rich solution using a syringe, surgical application, or application concomitant with another surgical procedure. It should be understood, however, that step 150 may comprise any biomedically acceptable process or procedure by which the IL-1ra-rich solution is implanted, injected, or otherwise administered into or in proximity to a site in order to mediate effects related to stimulation of the interleukin-1 receptor, such as inflammation. For example, for treating inflammation caused by arthritis, an autologous IL-1ra-rich solution may be administered to the patient via injection. Injection may be located at or into the synovial space of an inflamed joint, or otherwise at or near the joint.

The present technology further provides methods for delivering IL-1ra. Such delivery methods provide a solution of IL-1ra and fibrinogen where the fibrinogen is activated to form a fibrin matrix that protects and retains the IL-1ra at a treatment site. The fibrin matrix can be formed in situ upon delivery of the IL-1ra.

Fibrinogen can be cross-linked into a three-dimensional matrix by activation with a clotting agent and calcium. Suitable clotting agents include thrombin (e.g., bovine, recombinant human, pooled human, or autologous), autologous clotting protein, and polyethylene glycol. Calcium may be in the form of a calcium salt, such as calcium chloride.

Figure 4:
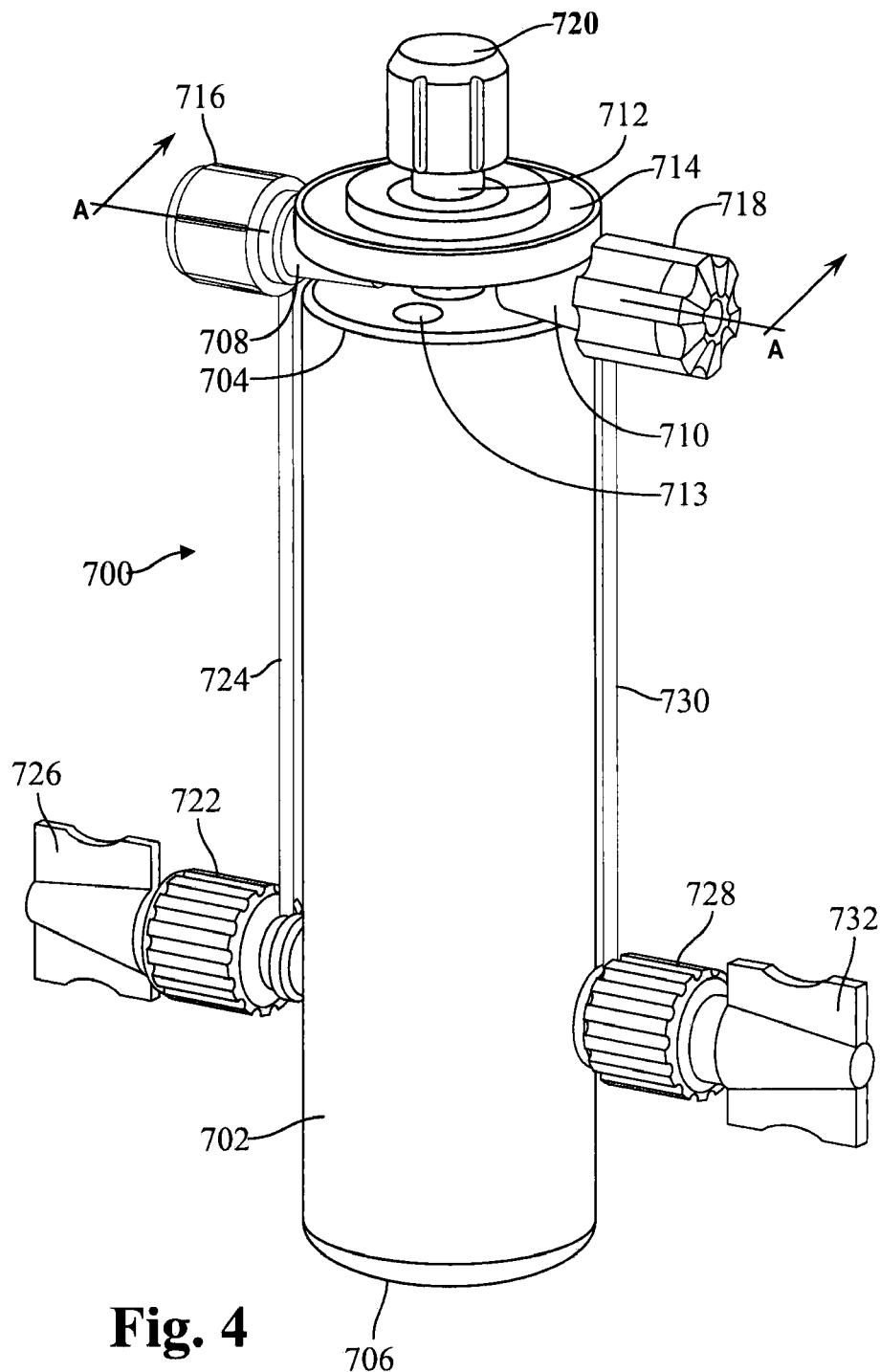
FIG. 4 is blood component isolation device which may be used in methods of the present technology.
Figure 5:
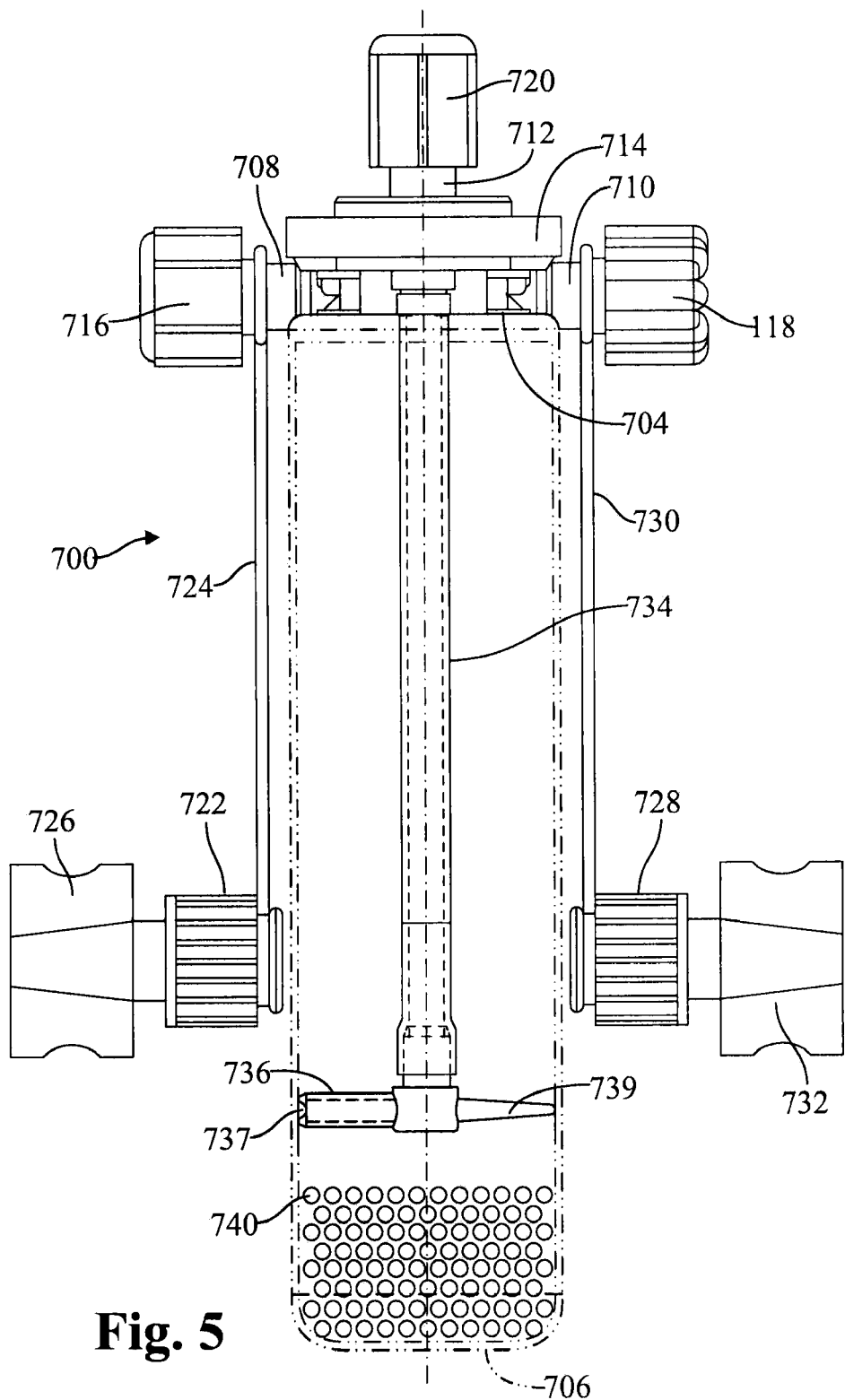
FIG. 5 is a side view of the blood component isolation device of FIG. 4, illustrating an interior portion of a main chamber of the device.

In some embodiments, the clotting agent comprises an autologous clotting protein, as a clotting fraction or composition derived from blood obtained from the patient to be treated. A suitable clotting fraction can be obtained by a process of: loading whole blood or plasma with a calcium solution (e.g., calcium chloride in ethanol) into a blood isolation device; heating the whole blood or plasma for at least about 20 minutes, at a temperature of at least about 20° C.; and isolating the clotting fraction. The isolating may be performed by centrifuging the heated whole blood or plasma. A suitable isolation device is depicted in FIGS. 4 and 5. Such a device is available as the Clotalyst™ Autologous Thrombin Collection System from Biomet Biologics LLC, Warsaw, Ind., USA.

With reference to FIGS. 4 and 5, the blood separation device 700 generally includes a body having a cylindrical wall along with a first end 704 and a second end 706 that define a main chamber 702. At the first end 704 is a first port 708, a second port 710, a third port 712, a vent 713, and a filter 714. Each of the first port 708, the second port 710, the third port 712, and the vent 713 extend through the first end 704 and permit fluid communication between an exterior of the device 700 and the main chamber 702. The first port 708 can be covered with a first cap 716, the second port 710 can be covered with a second cap 718, and the third port 712 can be covered with a third cap 720. A first replacement cap 722 for the first port 708 can be attached to the first port 708 with a first tether 724. A first cover 726 can be secured to the first replacement cap 722 when the first replacement cap 722 is not in use. A second replacement cap 728 for the second port 710 can be attached to the second port 710 with a second tether 730. A second cover 732 can be secured to the second replacement cap 728 when the second replacement cap 128 is not in use.

The first port 708 and the second port 710 each include a stop valve to prevent materials, such as glass beads 740, from exiting the main chamber 702 through the first and the second ports 708 and 710. The valves can be any suitable valve, such as a duck-billed valve.

With particular reference to FIG. 5, the third port 712 includes an elongated tube portion 734 that extends within the main chamber 702. The elongated portion 734 extends from the first end 704 to a depth within the main chamber 702 to permit withdrawal of select materials, such as thrombin and other blood clotting factors, from within the main chamber 702. For example and as further described below, where the main chamber 702 includes whole blood, reagents (e.g., a calcium solution comprising calcium compound dissolved in ethanol or other suitable solvent), anticoagulant, and glass beads, incubation and centrifugation of this mixture forms a clotted mass of about including red blood cells, blood plasma, and glass beads at the second end 706 of the main chamber 702. On top of the clotted mass, at the side of the clotted mass nearest the first end 704, an effluent is formed comprising thrombin and various other clotting factors. The clotted mass at the second end 706 can be visually distinguished from the effluent. In order to extract thrombin and the other clotting factors using the elongated tube portion 734, the elongated tube portion 734 extends to a depth within the main chamber 702 that is approximately level with the portion of the effluent closest to the clotted mass.

A tip 736 is provided at a distal end of the elongated portion 734. The tip 736 extends from the elongated portion 734 at about a right angle. The tip includes a recess or notch 737. Two support posts 739 extend radially from the elongated portion 734 approximately at the tip 736 to contact an interior of the main chamber 702. The support posts 739 bias the tip 736 against the interior of the main chamber 702 to retain the tip 736 at a constant position in the main chamber 702. While the tip 736 contacts the interior of the main chamber 702, the notch 737 provides an opening or clearance between the interior wall of the main chamber 702 and the tip 736 to permit the passage of material through the notch 737 and into the tip 736. The tip 736 helps to maximize the amount of materials withdrawn through the elongated portion 734, particularly when the main chamber 702 is tilted to bring additional materials surrounding the tip 736 to the notch 737. The two support posts 739 and the tip 736 help center the elongated portion 734 in the main chamber 702.

The ports 708, 710, and 712 are sized to cooperate with a suitable fluid delivery or transport device, such as a syringe. For example, the first port 708 can be sized to cooperate with a reagent syringe to permit passage of reagent through the first port 708 and into the main chamber 702; the second port 710 can be sized to cooperate with a blood syringe to permit passage of blood through the second port 710 and into the main chamber 702; and the third port 712 can be sized to cooperate with a syringe to permit withdrawal of blood components, such as thrombin and other clotting factors, from within the main chamber 702.

The filter 714 can be any suitable filter for filtering materials as they are withdrawn from within the main chamber 702 through the third port 712. The filter 714 includes a polyester screen that is mounted atop the first port 708 and the second port 710. The polyester screen includes openings that are in the range of about 15 microns to about 25 microns in size. For example, the openings can be about 17 microns in size. In place of or in addition to, the filter 714, a filter similar to the filter 714 can be provided in the elongated portion 734 or at the tip 736.

The main chamber 702 further includes an activator, such as glass beads 740. The negatively charged surface of the glass beads activates clotting and the release of blood clotting factors, which form the clotted mass at the second end 706 of the main chamber 702. The glass beads 740 can be any suitable type of glass beads, such as boro-silicate beads.

An exemplary procedure for producing a clotting agent using the device of FIG. 5 begins by injection of a reagent comprising calcium chloride and ethanol into the main chamber 702 through the first port 708. After the reagent has been injected, the first port 708 is closed using the first replacement cap 722. Blood with anticoagulant is injected into the main chamber 702 through the second port 710. After the blood has been injected, the second port 710 is closed using the second replacement cap 728. Optionally, the syringes and blood separation device 700 are pre-heated to a temperature of about 25° C.

The contents of the blood component separation device 700 are mixed by repeatedly inverting the device 700, e.g. about twelve times, so as to contact the blood with the glass beads. After mixing, the device is incubated The incubation process can be at a temperature and for a duration that will permit the contents of the device 700 to be heated at about 25° C. for about 15 minutes. Upon completion of the incubation period, a clotted mass of red blood cells, blood plasma, and glass beads forms at the second end 706 of the main chamber 702. After incubation is complete, the device 700 is shaken enough to dislodge and break-up any gel that may be present. The device 700 is then placed in a suitable centrifuge and spun at about 3200 RPM for about 15 minutes to separate thrombin from the remaining blood components. After centrifugation, an effluent of thrombin and other clotting factors separates from the clotted mass. After centrifugation is complete, the third cap 720 is removed and a suitable extraction device, such a syringe, is used to remove the effluent of thrombin and other clotting factors from within the main chamber 702 by way of the third port 712, the elongated portion 734, and the tip 736.

Thus, the delivery method of the present technology may include administration of IL-1ra, fibrinogen, thrombin, and calcium to form a fibrin matrix at the treatment site. Exogenous fibrinogen may be added to a solution of IL-1ra, for example such as bovine thrombin, preferably at 1000 U/mL. Or, the IL-1ra solution may already have an adequate amount of endogenous fibrinogen. In the case where the solution of IL-1ra and/or fibrinogen or preparation thereof includes an anticoagulant, such as ACD-A (anticoagulant citrate dextrose solution), the addition of calcium (with thrombin) to activate the fibrinogen should exceed the effective amount of any chelator in the anticoagulant.

The IL-1ra-rich solutions prepared using the present methods can provide an increased concentration of endogenous fibrinogen relative to whole blood when whole blood and/or platelet-rich plasma is further added to the adipocytes and/or adipose tissue and the polyacrylamide beads. For example, output of the above methods employing platelet-rich plasma, adipose tissue, polyacrylamide beads, and the device illustrated in FIG. 3 results in a solution rich in both IL-1ra and fibrinogen relative to whole blood. Such a device is commercially available as the Plasmax™ Plus Plasma Concentrator, from Biomet Biologics, LLC (Warsaw, Ind., USA) and includes those devices and methods of use described in U.S. Application Publication 2006/0175268, Dorian et al., published Aug. 10, 2006; and U.S. Application Publication 2006/0243676, Swift et al., published Nov. 2, 2006; both of which are incorporated by reference herein. This IL-1ra-rich and fibrinogen-rich solution may be used to treat the patient from which the original whole blood and adipose tissue were derived; i.e., autologous treatment.

An IL-1ra-rich and fibrinogen-rich solution, prepared using the above methods using whole blood, adipose tissue, and polyacrylamide beads with the Plasmax™ Plus Plasma Concentrator, provides a solution having about a 3-fold (3×) increase in fibrinogen concentration relative to whole blood. The fibrin matrix/clot formed from the 3× higher concentration of fibrinogen is more substantial than a fibrin clot made from baseline fibrinogen levels and is more resistant to breakdown and resorption.

Figure 6:
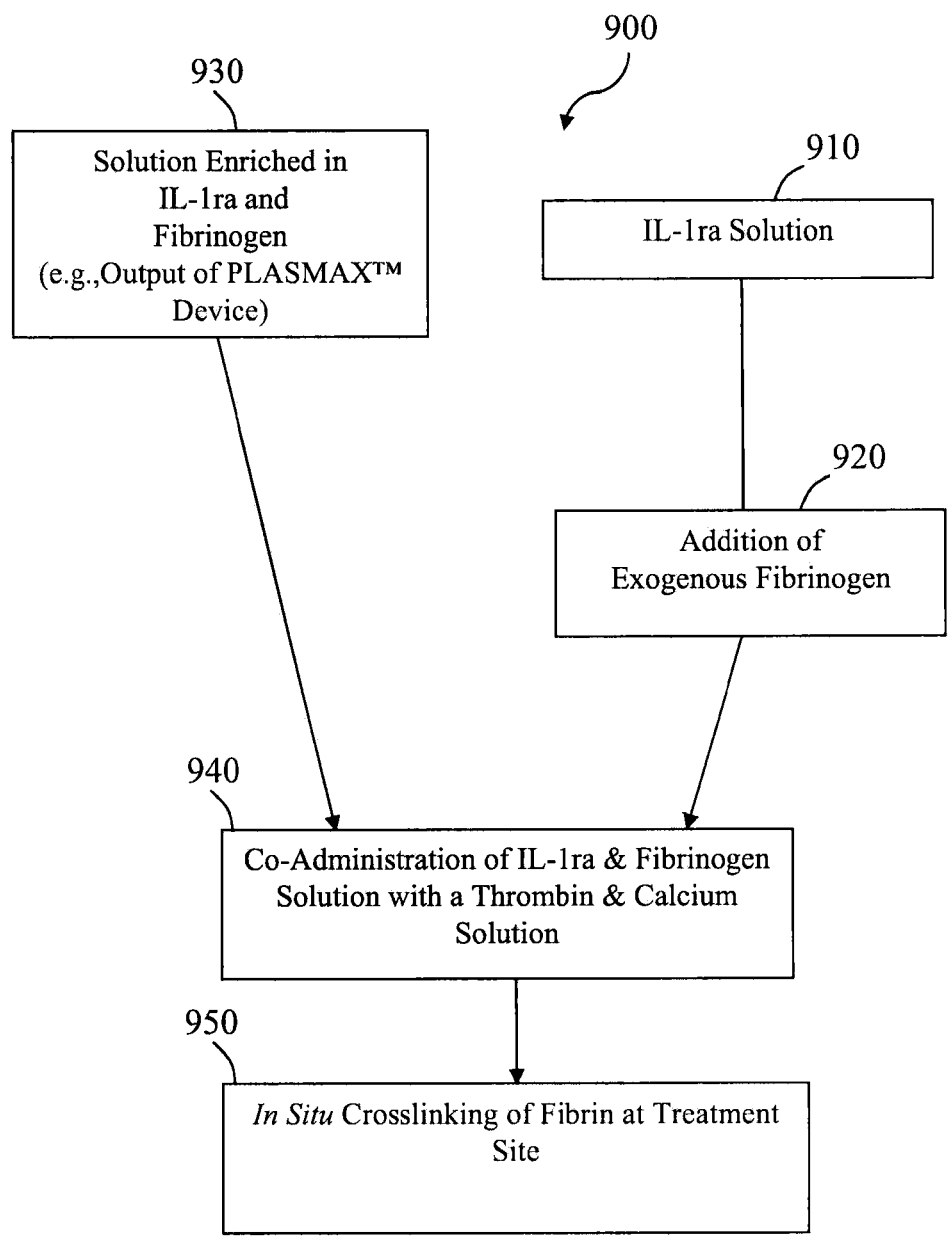
FIG. 6 is a diagrammatic illustration of a method for delivering IL-1ra according to an embodiment of the present technology.

Referring to FIG. 6, a diagrammatic illustration for delivering IL-1ra 900 is shown. At step 910, a solution of IL-1ra is provided. The IL-1ra solution may be prepared using the methods described in the present disclosure. Exogenous fibrinogen is added to the IL-1ra solution in step 920. The exogenous fibrinogen may be prepared from a different source than the IL-1ra solution, such as a different patient, or may be bovine in origin. Or, the exogenous fibrinogen may be prepared from different starting material than the IL-1ra solution, but still from the same source or patient. For example, the IL-1ra solution and the exogenous fibrinogen may be prepared from different blood samples taken from the same patient. Alternatively, as shown in step 930, a solution that is enriched in both IL-1ra and fibrinogen is prepared, for example, by using polyacrylamide beads and the Plasmax™ device, as described herein. A solution of thrombin and calcium is provided in step 940 and is co-administered with the solution of IL-1ra to a treatment site. Thereafter, as shown in step 950, the fibrin in the combined solutions cross-links in situ, forming a matrix at the treatment site that serves to protect, retain, and slow release of the IL-1ra.

Delivery of IL-1ra may include co-administering a first solution of IL-1ra and fibrinogen and a second solution of thrombin and calcium to a subject. In such embodiments, the first solution and second solution are kept separate until administered so that the fibrinogen does not form a fibrin matrix until after the solutions are mixed and injected into a treatment site. The solutions may be mixed just before delivery to the treatment site or may be mixed at the treatment site.

Figure 7:
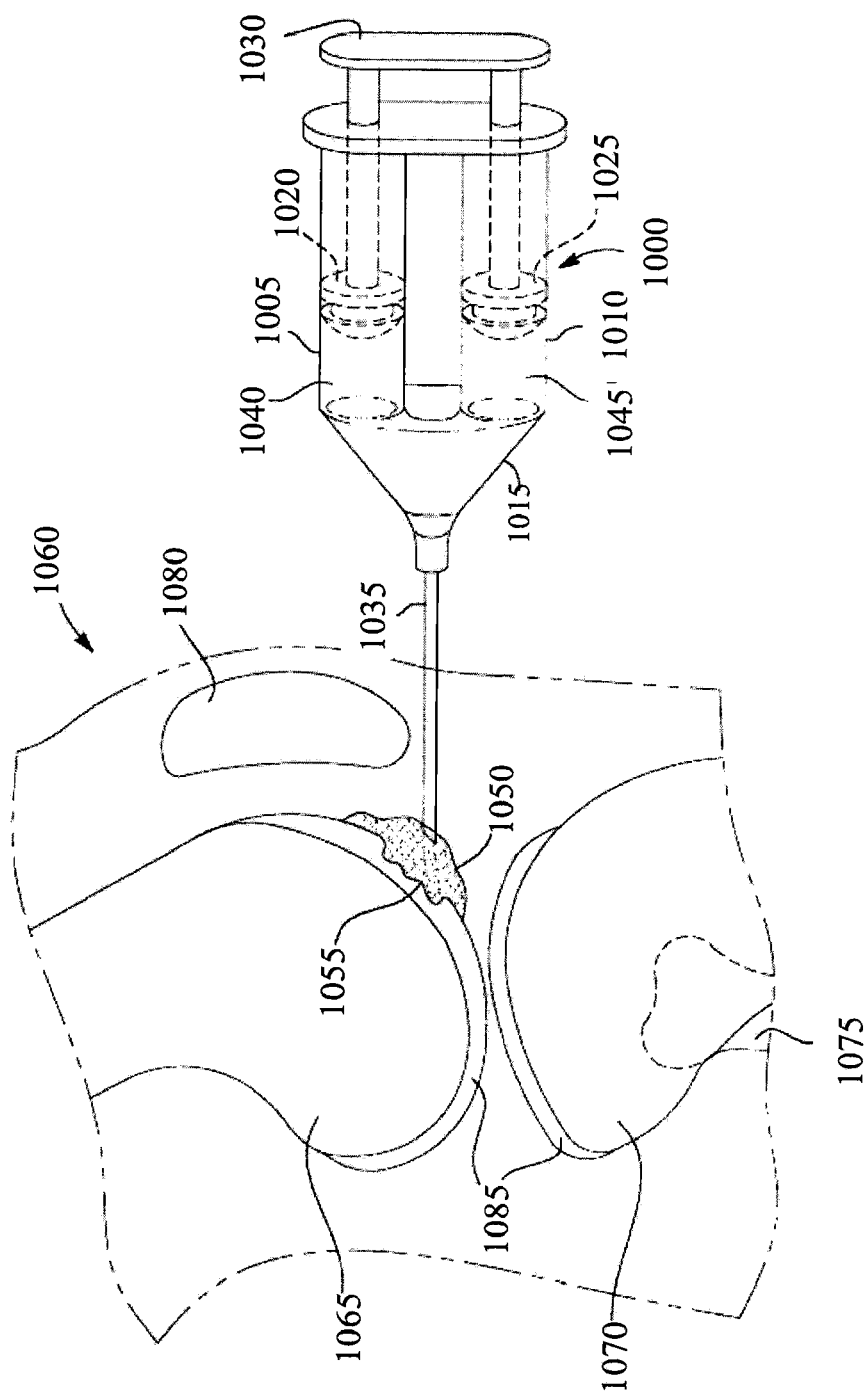
FIG. 7 is a partial cross-sectional view of a representative device for delivering IL-1ra according to one embodiment of the present technology.

Referring to FIG. 7, a dual syringe device 1000 may be employed in a medically appropriate procedure. The dual syringe device 1000 includes a first barrel 1005 and a second barrel 1010, both of which are connected to a mixing chamber 1015. A first plunger 1020 is inserted into the first barrel 1005 and a second plunger 1025 is inserted into the second barrel 1010. The first plunger 1020 and the second plunger 1025 are connected by a member 1030. The mixing chamber 1015 connects to a cannula 1035. The dual syringe device 1000 contains a first solution 1040 of IL-1ra and fibrinogen in the first barrel 1005, and a second solution 1045 of thrombin and calcium in the second barrel 1010. During co-administration, member 1030 is pushed toward the mixing chamber 1015 such that the contents of both the first barrel 1005 and the second barrel 1010 are pushed into the mixing chamber 1015. The mixed first solution 1040 and second solution 1045 travel through the cannula 1035 and form a fibrin-matrix 1050 at the treatment site 1055 within a patient's joint 1060.

In the embodiment shown in FIG. 7, the patient's joint 1060 is a knee joint that includes a femur 1065, a tibia 1070, a fibula 1075, a patella 1080, and cartilage 1085. It should be understood, however, that the treatment site 1055 may be in any joint of a human patient or animal, including shoulders, elbows, wrists, ankles, hips, and the spinal column. In addition, the present methods may be used to treat inflammation in sites within other tissues, such as muscle and tendon.

In some embodiments, the dual syringe device 1000 is used to pierce soft tissue of the patient's joint 1060 to administer the mixed first solution 1040 and second solution 1045. For example, the cannula 1035 may be a hollow needle such as a hypodermic needle. Alternatively, an incision may be made in the patient's joint 1060 to allow entry of the cannula 1035 so that the dual syringe device 800 may enter the treatment site 1055.

In some embodiments, which are not shown, the dual syringe device 1000 does not have a mixing chamber 1015 and instead includes two cannulas 1035, one leading from each barrel to the treatment site 1055. In this case, the first solution 1040 and second solution 1045 travel through the separate cannulas 1035 and mix together at the treatment site 1055 to form a fibrin-matrix 1050. In some embodiments, two separate single-barreled syringe devices are employed in place of a dual syringe device.

The fibrin matrix formed in the present delivery methods can reside at the treatment site without increasing inflammation. The IL-1ra within the fibrin matrix is protected from enzymatic degradation and may bind to the fibrin matrix so that is it slowly released from the matrix over time. The methods consequently can provide sustained delivery of IL-1ra as compared to injection of IL-1ra without the fibrin-matrix carrier.

The present technology can include aspects of U.S. Provisional Application No. 61/031,803 filed Feb. 27, 2008, U.S. Provisional Application No. 61/116,940 filed Nov. 21, 2008, and U.S. Provisional Application No. 61/155,048 filed Feb. 24, 2009 and includes aspects of PCT/US2009/035541 filed Feb. 27, 2009.

The following specific examples are provided for illustrative purposes of how to make and use the compositions and methods of this technology and, unless explicitly stated otherwise, are not intended to be a representation that given embodiments of this technology have, or have not, been made or tested.

Example 1

Adipocytes are prepared as follows. Adipose tissue is minced into small pieces (about 1 cm$^3$) and digested in 2 mg/mL type I collagenase (Worthington Biochemical Corp., Lakewood, N.J.) under intermittent mechanical agitation in a water bath at 37° C. for 180 minutes. Digestion can be neutralized by the addition of medium or a blood-derived solution. The cell suspension is centrifuged (300×g for 7 minutes at 25° C.) followed by removal of the supernatant from the cell pellet. The pellet is then resuspended in a compatible solution to provide a liquid volume comprising adipocytes.

Alternatively, the pellet is suspended with whole blood obtained from the subject, and added to a GPS™ Platelet Concentrate System, from Biomet Biologics, Inc. (Warsaw, Ind.). Following centrifugation, the platelet-rich plasma layer, which also contains the adipocytes, is extracted from the system.

The adipocytes, optionally including platelet-rich plasma, are then combined with polyacrylamide beads to stimulate production of IL-1ra. The adipocytes and polyacrylamide beads are separated from the liquid solution to obtain a solution rich in IL-1ra.

Example 2

A therapeutic composition of IL-1ra is generated from adipocytes. Isolation of human adipocytes is performed by obtaining human subcutaneous adipose tissue from lipoaspiration/liposuction procedures and digesting the tissue in collagenase type I solution (Worthington Biochemical Corp., Lakewood, N.J.) under gentle agitation for 1 hour at 37° C. The dissociated cells are filtered with 500 µm and 250 µm Nitex filters. The fraction is centrifuged at 300×g for 5 minutes. The supernatant is discarded and the cell pellet is resuspended in a compatible liquid solution, such as a blood-derived solution.

The adipocytes are combined with polyacrylamide beads in a device such as shown in FIGS. 3A and 3B. A fluid 355 containing the adipocytes is injected to the upper chamber via the inlet port 330 and mixed with the polyacrylamide beads 350. The fluid 355 and polyacrylamide beads 350 may be mixed by rotating the agitator stem 320 and the gel bead agitator 325, to help mix the fluid 355 and beads 350. The mixed fluid 355 and polyacrylamide beads 350 are then incubated for the desired time at the desired temperature. The device 300 is then centrifuged so that liquid passes to the lower chamber 310 while the polyacrylamide beads 350 are retained by a filter 345, thereby separating the polyacrylamide beads 350 from the resulting solution 360 of IL-1ra that collects in the lower chamber 310. The IL-1ra rich solution 360 may be removed from the device via outlet port 335.

Example 3

An IL-1ra-rich solution is created as follows. Adipose tissue is harvested by liposuction from a patient. Whole blood (70 mL) anticoagulated (10%) with ACD-A (Braintree, Mass., USA) is drawn from the patient. A portion (10 mL) is reserved for a whole blood measurement. Platelet-rich plasma (PRP) (6 mL) is produced using the GPS® II System (Biomet Biologics, LLC, Warsaw, Ind., USA). Complete blood counts (CBC) are collected for the whole blood and PRP samples following a validated procedure, as described in Woodell-May J E, Ridderman D N, Swift M J, Higgins J. "Producing Accurate Platelet Counts for Platelet Rich Plasma: Validation of a Hematology Analyzer and Preparation Techniques for Counting" *J Craniofac Surg* (2005) September 16(5):749-56.

Adipose tissue (about 5 grams) and PRP (about 5 mL) are added to a modified plasma concentration device (Plasmax™, Biomet Biologics LLC, Warsaw, Ind., USA) and incubated with polyacrylamide desiccating beads in the device for 24 hours at room temperature. Following incubation, the plasma concentration device is centrifuged to separate the solution rich in IL-1ra.

To analyze baseline IL-1ra levels at time zero, the adipose tissue, PRP, and polyacrylamide samples are activated with 50 µL of thrombin and 10% $CaCl_2$ (1,000 units/mL). A blood clot is formed and incubated for 30 minutes at room temperature. Following incubation, the clot is centrifuged for 5 minutes at 3,000 rpm. Serum is collected from the clots and retained for ELISA analysis. The IL-1ra rich solution from the plasma concentrator does not require activation by thrombin, and is tested directly. All samples are analyzed for IL-1ra using an ELISA kit (IL-1ra Quantikine™ Kit, R&D Systems, Minneapolis, Minn., USA).

Illustrative data is presented as mean±standard deviation. Statistical significance is evaluated with a Student's t-test (a=0.05). A correlation analysis is used to compare IL-1ra output and complete blood counts (CBC) data.

IL-1ra generated from incubation of adipose tissue and PRP with polyacrylamide beads provides an increased level of IL-1ra. The baseline serum values of IL-1ra (217±98 pg/mL) are similar to results found in another study (73±4.8 pg/mL), described in Meijer H, Reinecke J, Becker C, Tholen G, Wehling P. "The production of anti-inflammatory cytokines in whole blood by physico-chemical induction" *Inflamm. Res.* 2003 October; 52(10):404-7, even though significant variability between donors can exist. The IL-1ra serum levels are statistically higher in output of the plasma concentrator following incubation of adipose tissue and PRP with polyacrylamide beads compared to the baseline serum levels. For example, 24-hour incubation of the adipose tissue and PRP with polyacrylamide beads in the plasma concentration device results in a dose of IL-1ra (about 36,000 pg/mL) that is higher than the previously reported data from the 24-hour incubation in the ACS device (10,254±165 pg/mL).

Example 4

Adipose tissue (120 g) is collected and prepared using GPS®III disposables (Biomet Biologics LLC, Warsaw, Ind., USA). The isolated adipose tissue is loaded into modified plasma concentration devices (Plasmax®, Biomet Biologics LLC, Warsaw, Ind., USA) and processed. The output is divided into 4 groups; IL-1ra in concentrated plasma with and without thrombin activation (1000 U/ml in 1 M $CaCl_2$), or cell-free IL-1ra with and without thrombin activation. IL-1ra is measured using ELISA (R&D Systems) over time.

Unclotted samples produce an average of 47.1±2.1 ng over 24 hrs (p=0.34). The cell-free samples produce 33.7±1.5 ng without changing over 24 hrs (p=0.38). Once clotted, the elution of IL-1ra is slowed, with only 28% being eluted after 10 hours. Release in the cell-free samples is also delayed, but eluted 100% of available IL-1ra after 10 hours.

The examples and other embodiments described herein are exemplary and not intended to be limiting in describing the full scope of compositions and methods of the present technology. Equivalent changes, modifications and variations of specific embodiments, materials, compositions and methods may be made within the scope of the present technology, with substantially similar results.

What is claimed is:

1. A method for generating a solution rich in interleukin-1 receptor antagonist comprising: (a) contacting isolated adipose tissue with polyacrylamide beads, wherein the polyacrylamide beads activate the isolated adipose tissue to produce interleukin-1 receptor antagonist to form a solution rich in interleukin-1 receptor antagonist; and (b) separating the solution rich in interleukin-1 receptor antagonist from the isolated adipose tissue and the polyacrylamide beads.

2. The method for generating a solution rich in interleukin-1 receptor antagonist according to claim 1, wherein the contacting comprises incubating the isolated adipose tissue with the polyacrylamide beads for a time of from about 30 seconds to about 24 hours.

3. The method for generating a solution rich in interleukin-1 receptor antagonist according to claim 1, wherein the contacting further comprises contacting a liquid volume comprising white blood cells with the polyacrylamide beads.

4. The method for generating a solution rich in interleukin-1 receptor antagonist according to claim 3, wherein the liquid volume comprising white blood cells is whole blood, platelet rich plasma, or whole blood and platelet rich plasma.

5. The method for generating a solution rich in interleukin-1 receptor antagonist according to claim 1, wherein the separating comprises centrifuging the isolated adipose tissue and polyacrylamide beads to obtain a supernatant comprising the solution rich in interleukin-1 receptor antagonist.

6. The method for generating a solution rich in interleukin-1 receptor antagonist according to claim 1, wherein the solution rich in interleukin-1 receptor antagonist comprises from about 30,000 pg/mL to about 110,000 pg/mL interleukin-1 receptor antagonist.

7. A method for generating a solution rich in interleukin-1 receptor antagonist for treating an inflammatory disorder in a patient, the method comprising: (a) obtaining adipose tissue from the patient; (b) loading the adipose tissue into a concentrator assembly including polyacrylamide beads and incubating the mixture of polyacrylamide beads and adipose tissue to form a solution of interleukin-1 receptor antagonist; and (c) rotating the concentrator assembly at centrifugal speeds to separate the interleukin-1 receptor antagonist from the polyacrylamide beads and adipose tissue to obtain the solution rich in interleukin-1 receptor antagonist.

8. The method for generating a solution rich in interleukin-1 receptor antagonist according to claim 7, wherein the loading comprises incubating the adipose tissue with the polyacrylamide beads for a time of from about 30 seconds to about 24 hours.

9. The method for generating a solution rich in interleukin-1 receptor antagonist according to claim 7, wherein the loading further comprises loading a liquid volume comprising white blood cells into the concentrator assembly.

10. The method for generating a solution rich in interleukin-1 receptor antagonist according to claim 9, wherein the liquid volume comprising white blood cells is whole blood, platelet rich plasma, or whole blood and platelet rich plasma.

* * * * *

UNITED STATES PATENT AND TRADEMARK OFFICE
CERTIFICATE OF CORRECTION

| | | |
|---|---|---|
| PATENT NO. | : 8,753,690 B2 | Page 1 of 1 |
| APPLICATION NO. | : 12/549015 | |
| DATED | : June 17, 2014 | |
| INVENTOR(S) | : Higgins et al. | |

It is certified that error appears in the above-identified patent and that said Letters Patent is hereby corrected as shown below:

Title Page 2:

Column 1, OTHER PUBLICATIONS, Line 3, delete "Bruchure" and insert therefor --Brochure--.

In the Specification:

Column 7, Line 9, delete "N,N" and insert therefor --N,N'--.

Column 12, Line 6, delete "128" and insert therefor --728--.

Column 15, Line 12, delete "800" and insert therefor --1000--.

Column 15, Line 20, delete "1050," and insert therefor --1050.--.

Signed and Sealed this
Twenty-first Day of October, 2014

Michelle K. Lee
*Deputy Director of the United States Patent and Trademark Office*